United States Patent
Sternby et al.

(10) Patent No.: US 6,726,647 B1
(45) Date of Patent: Apr. 27, 2004

(54) METHOD AND DEVICE FOR MEASURING ACCESS FLOW

(75) Inventors: Jan Peter Sternby, Lund (SE); Gary Joel Mishkin, Potomac, MD (US); Perry Asbrink, Malmo (SE); Eddie Nilsson, Sosdala (SE)

(73) Assignee: Gambro AB, Stockholm (SE)

( * ) Notice: Subject to any disclaimer, the term of this patent is extended or adjusted under 35 U.S.C. 154(b) by 0 days.

(21) Appl. No.: 09/425,124

(22) Filed: Oct. 22, 1999

Related U.S. Application Data
(60) Provisional application No. 60/105,396, filed on Oct. 23, 1998.

(51) Int. Cl.$^7$ .............................. A61M 37/00; C02F 1/44
(52) U.S. Cl. ........................ 604/6.09; 210/646; 210/739
(58) Field of Search .............................. 604/4.01, 5.01, 604/6.09, 6.11; 210/739, 746, 645–647; 73/1.16, 195, 196; 600/322, 328

(56) References Cited

U.S. PATENT DOCUMENTS

| 1,441,088 A | 1/1923 | Hofstetter |
| 2,352,629 A | 7/1944 | Griswold |
| 2,709,785 A | 5/1955 | Fielden |

(List continued on next page.)

FOREIGN PATENT DOCUMENTS

| EP | 0097366 | 1/1984 |
| EP | 0272414 | 6/1988 |
| EP | 0693296 A1 | 1/1996 |
| EP | 0773035 A2 | 5/1997 |
| EP | 0773035 A3 | 11/1997 |
| EP | 0845273 A1 | 6/1998 |
| EP | 0928614 | 7/1999 |
| EP | 0928614 A1 | 7/1999 |
| EP | 0995451 | 4/2000 |
| ES | 2026508 | 5/1992 |
| FR | 2804609 | 2/2000 |
| GB | 2093192 | 8/1982 |
| JP | 36990/77 | 10/1977 |
| JP | 190873/85 | 9/1985 |
| SU | 521891 | 10/1976 |
| SU | 10/3853 | 4/1983 |

(List continued on next page.)

OTHER PUBLICATIONS

Jeffrey Sands et al.,"The Effect of Doppler Flow Screening Studies and Elective Revisions on Dialysis Access Failure", Reprint from ASAIO Transactions, Jul.–Sep., 1992, pp. M524–M527.

John L. Nosher, "Death Taxes, and Vascular Access Dysfunction, Seminars in Dialysis," vol. 4, No. 2, pp. 67–68, Apr.–Jun. 1991, New Jersey.

In–Line Diagnostics (brochure) "Improve the Clinical Outcome of Every Patient!", four pages, (undated).

(List continued on next page.)

*Primary Examiner*—Angela D. Sykes
*Assistant Examiner*—Leslie Deak
(74) *Attorney, Agent, or Firm*—Edna M. O'Connor; Laura M. Butterfield

(57) ABSTRACT

An arterial needle removes blood from the access to an extracorporeal circuit comprising a dialyzer and a venous needle returns the blood to the access site. Blood passes along one side of the membrane of the dialyzer and dialysis fluid along the other side. The concentration (Cd norm and Cd rev) of urea in the dialysate emitted from the dialyzer is measured with the needles in the normal position and in a reversed position. The access flow rate before the arterial needle is calculated according to the formula:

$$Cd\ norm/Cd\ rev = 1 + Keff/Qa$$

in which Keff is the effective clearance of the dialyzer and Qa is the access flow rate.

27 Claims, 6 Drawing Sheets

U.S. PATENT DOCUMENTS

| | | |
|---|---|---|
| 2,865,402 A | 12/1958 | Miller |
| 3,080,887 A | 3/1963 | Brandenberg |
| 3,157,201 A | 11/1964 | Littmann |
| 3,324,720 A | 6/1967 | Suterland |
| 3,396,331 A | 8/1968 | Sperry, III |
| 3,404,336 A | 10/1968 | Rosenthal |
| 3,450,984 A | 6/1969 | Holmes |
| 3,482,575 A | 12/1969 | Claff et al. |
| 3,491,592 A | 1/1970 | Evers et al. |
| 3,585,995 A | 6/1971 | Perkins et al. |
| 3,586,049 A | 6/1971 | Adamson |
| 3,619,423 A | 11/1971 | Galletti et al. |
| 3,626,938 A | 12/1971 | Versaei |
| 3,678,960 A | 7/1972 | Leibinsohn |
| 3,722,276 A | 3/1973 | Chandler et al. |
| 3,733,965 A | 5/1973 | Braun |
| 3,834,372 A | 9/1974 | Turney |
| 3,867,688 A | 2/1975 | Koski |
| 3,957,082 A | 5/1976 | Fuson et al. |
| 3,980,946 A | 9/1976 | Fleury |
| 3,985,134 A | 10/1976 | Lissot et al. |
| 3,987,788 A | 10/1976 | Emil |
| 4,037,622 A | 7/1977 | Osheroff et al. |
| 4,081,372 A | 3/1978 | Atkin et al. |
| 4,098,275 A | 7/1978 | Consalvo |
| 4,113,614 A | 9/1978 | Rollo et al. |
| 4,136,563 A | 1/1979 | Mueller et al. |
| 4,138,639 A | 2/1979 | Hutchins |
| 4,177,677 A | 12/1979 | Ruzicka et al. |
| 4,181,610 A | 1/1980 | Shintani et al. |
| 4,256,135 A | 3/1981 | Hannah |
| 4,361,049 A | 11/1982 | Volgyesi |
| 4,446,871 A | 5/1984 | Imura |
| 4,464,164 A | 8/1984 | Troutner et al. |
| 4,490,134 A | 12/1984 | Troutner |
| 4,490,135 A | 12/1984 | Troutner |
| 4,508,622 A | 4/1985 | Polaschegg et al. |
| 4,593,717 A | 6/1986 | Levasseur |
| 4,650,458 A | 3/1987 | Dahlberg et al. |
| 4,738,265 A | 4/1988 | Ritchart et al. |
| 4,739,492 A | 4/1988 | Cochran |
| 4,740,755 A | 4/1988 | Ogawa |
| 4,825,168 A | 4/1989 | Ogawa et al. |
| 4,885,087 A | 12/1989 | Kopf |
| 4,898,669 A | 2/1990 | Tesio |
| 4,995,268 A | 2/1991 | Ash et al. |
| 5,004,459 A | 4/1991 | Peabody et al. |
| 5,024,756 A | 6/1991 | Sternby |
| 5,058,416 A | 10/1991 | Engelhardt et al. |
| 5,092,836 A | 3/1992 | Polaschegg |
| 5,098,373 A | 3/1992 | Polaschegg |
| 5,312,550 A | 5/1994 | Hester |
| 5,372,136 A | 12/1994 | Steuer et al. |
| 5,442,969 A | 8/1995 | Troutner et al. |
| 5,443,453 A | 8/1995 | Walker et al. |
| 5,453,576 A | 9/1995 | Krivitski |
| 5,507,723 A | 4/1996 | Keshaviah |
| 5,510,716 A | 4/1996 | Buffaloe, IV et al. |
| 5,510,717 A | 4/1996 | Buffaloe, IV et al. |
| 5,518,623 A | 5/1996 | Keshaviah et al. |
| 5,588,959 A | 12/1996 | Ahmad et al. |
| 5,595,182 A | 1/1997 | Krivitski |
| 5,605,630 A | 2/1997 | Shibata |
| 5,662,806 A | 9/1997 | Keshaviah et al. |
| 5,685,989 A | 11/1997 | Krivitski et al. |
| 5,830,365 A | 11/1998 | Schneditz |
| 5,866,015 A | 2/1999 | Krämer |
| 5,894,011 A | 4/1999 | Prosl et al. |
| 5,902,336 A | 5/1999 | Mishkin |
| 6,098,576 A | 8/2000 | Nowak, Jr. et al. |
| 6,117,099 A | 9/2000 | Steuer et al. |
| 6,126,831 A | 10/2000 | Goldau et al. |
| 6,153,109 A | 11/2000 | Krivitski |
| 6,156,002 A * | 12/2000 | Polaschegg et al. ........ 210/646 |
| 6,158,965 A | 12/2000 | Butterfield et al. |
| 6,177,049 B1 * | 1/2001 | Schnell et al. ................ 422/44 |
| 6,189,388 B1 * | 2/2001 | Cole et al. .............. 73/861.07 |
| 6,210,591 B1 | 4/2001 | Krivitski |
| 6,221,040 B1 | 4/2001 | Kleinekofort |
| 6,258,027 B1 * | 7/2001 | Sternby ...................... 210/646 |
| 6,273,133 B1 | 8/2001 | Williamson et al. |
| 6,308,737 B1 | 10/2001 | Krivitski |
| 6,418,966 B2 | 7/2002 | Loo |
| 2001/0013370 A1 | 8/2001 | Loo |
| 2001/0031222 A1 | 10/2001 | Schnell et al. |
| 2002/0062098 A1 | 5/2002 | Cavicchioli et al. |

FOREIGN PATENT DOCUMENTS

| | | |
|---|---|---|
| WO | WO 9608305 A1 | 3/1996 |
| WO | WO 97/10013 | 3/1997 |
| WO | WO 98/17193 | 4/1998 |
| WO | WO 98/17334 | 4/1998 |
| WO | WO 98/32477 | 7/1998 |
| WO | WO 99/64088 | 12/1999 |
| WO | WO 00/18451 | 4/2000 |
| WO | WO00/24440 | 5/2000 |
| WO | WO 01/45770 | 6/2001 |

OTHER PUBLICATIONS

In–Line Diagnostics (brochure) "Non–Invasive Blood Volume Monitoring", two pages, 1994.

In–Line Diagnostics (brochure) "The Crit–Line System", two pages, (undated).

John D. Bower and Thomas G. Coleman, "Circulatory Function During Chronic Hemodialysis", vol. XV Trans. Amer. Soc. Artif. Int. Organs, 1969, pp. 373–377.

C. Aldridge, "The Use and Management of Arteriovenous Fistulae Fact and Fiction," EDTNA ERCA, Journal SVII–4, pp. 29–35, Oct. 1991, United Kingdom.

R.L. Hester et al., "Non–Invasive Measurement of Recirculation in Dialysis Patient," Abstract No. 7, Jul. 1992.

Robert L. Hester et al., "Non–Invasive Determination of Recirculation in the Patient on Dialysis," ASAIO Journal, pp. M190–M193, 1992, Mississippi.

R.N. Greenwood and W. R. Cattell, "Single Needle Dialysis," Journal of Medical Engineering & Technology, vol. 6, No. 3 (May/Jun. 1982), pp. 93–98.

K. Konner, H M Karnahl, "Transvenous Serial Xero–Arteriography: A New Non–Invasive Angiographic Method for AV–Fistulas in Haemodialysis Patients," Proc EDTA (1981) vol. 18, pp. 305–309.

L. Forsberg, T. Holmin and E. Linstedt, "Quantitative Doppler And Ultrasound Measurements in Surgically Performed Arteriovenous Fistulas Of The Arm," Acta Radiologica Diagnosis 21 (1980) Fasc.6, pp. 769–771.

Thomas A. Depner and Nikolai M. Krivitski, "Clinical Measurement of Blood Flow in Hemodialysis Access Fistulae and Grafts by Ultrasound Dilution," Jul. 27, 1995, ASAIO Journal, pp. 0018–0022.

Thomas A Depner et al., "Hemodialysis Access Recirculation Measured by Ultrasound Dilution", Jul. 27, 1995, ASAIO Journal, pp. 0022–0026.

N.M. Krivitski, "Novel Method to Measure Access Flow Duing Hemodialysis by Ultrasound Dilution(UD)", ASAIO Journal 1995.

Nikolai M. Krivitski, "Theory and Validation of Access Flow Measurement by Dilution Technique During Hemodialysis", Kidney International, vol. 48 (1985), pp. 244–250.

N.M. Krivitski, "Accuracy of Ultrasound Dilution Method to Measure Access Flow (AF) in Hemodialysis", XIIIth International Congress of Nephrology, Abstract, 1995.

Nikolai Krivitski, Ph.D. "New Method to Measure Recirculation (RC) and Access Flow During Hemodialysis (HD)" American Nephrology Nurses' Association 26th National Symposium Exhibitor Continuing Education Program, Abstract 1995.

T. Depner, "Changes in Access Blood Flow(Qac) and Appearance of Recirculation (RC) During Hemodialysis", XIIIth International Congress of Nephrology, Abstract., 1995.

T. A. Depner et al., "Hemodialysis Access Recirculation (RC) Measured by Ultrasound Dilution", ASAIOJournal 1995 Abstracts, Supplement of Jan.–Mar. 1995 vol. 41, No. 1, p. 80.

T.A. Depner and N.M. Krivitski, "Clinical Measurement of Blood Flow in Hemodialysis Access Fistulae and Grafts by Ultrasound Dilution", ASAIO Journal 1995 Abstracts, Supplement to Jan.–Mar. 1995 vol. 41, No. 1, p. 80.

Transonic Systems, Inc., "Recirculation, Access Flow Measurements," 1995, pp. 19–26.

N.M. Krivitski, "Cardiac Output Measurement in Extacorporeal Systems, by Ultrasound Velocity Dilution," ASAIO Abstracts, 1994, p. 82.

Gambro, "Fistula Assessment Monitor FAM10 Service Manual," approximately 1985, Sidcup, Kent, U.K>.

J.S. Gani et al., "Use of the Fistula Assessment Monitor to Detect Stenoses in Access Fistulae," (abstract) Australian Society of Nephrology, 1989, Australia.

Jonathan S. Gani, "Use of the fistual Assessment Monitor to Detect Stenoses in Access Fistulae," American Journal of Kidney Diseases, vol. XVII, No. 3, pp. 303–306, Mar. 1991, Newcastle, Australia.

R N Greenwood et al. "Assessment of Arteriovenous Fistulae From Pressure and Recirculation Studies. Clinical Experience in 186 Fistulae", Abstract pg. 106, 1985, London, U.K.

R. N. Greenwood et al. "Assessment of Arteriovenous Fistulae From Pressure and Recirculation Studies: Clinical Experience in 215 Upper Limb Fistulas, EDTA–ERA", vol. 22, pp. 296–302, 1985, London, U.K.

R N Greenwood et al. "Assessment of Arteriovenous Fistulae From Pressure and Thermal Dilution Studies: Clinical Experience in Forearm Fistulae," Clinical Nephrology, vol. 23, No. 4, pp. 189–197, 1985, U.K.

L. Goldstein et al., The Assessment of Arteriovenous Fistulae From Pressure and Recirculation Studies:, Porc EDTNA–ERCA, vol. 14, pp. 207–215, 1985, United Kingdom.

Lynn W. Hart et al., A Noninvasive Electromagnetic Conductivity Sensor for Biomedical Applications:, IEEE Transactions on Biomedical Engineering, vol. 35, No. 12, pp. 1011–1022, Dec. 1988, Maryland.

Robert L. Hester et al., "The Determination of Hemodialysis Blood Reciruclation Using Blood Urea Nitrogen Measurements" American Journal of Kidney Diseases, vol. XX, No. 6, pp. 598–602, Dec. 1992, Mississippi.

M. Kramer et al., "Automated Measurement of Recirculation," EDTNA–ERCA, Journal, vol. XIX, No. 2, Apr. 1993.

Matthias Kramer et al., "A Device for Control of Thermal Parameters and Recirculation Measurement in Hemodialysis," Nov., 1992, Germany.

Transonic Systems, Inc., "Transonic Hemodialysis Monitor Measures Access Flow Recirculation Cardiac Output Routinely during Dialysis," Apr. 1995.

Nikolai M. Krivitski, "Novel Method to Measure Access Flow During Hemodialysis by Ultrasound Velocity Dilution Technique", Jul. 27, 1995, ASAIO Journal, pp. 0014–0018.

Robert L. Hester, Ph.D., "A New Technique for Determining Recirculation in the ESRD Patient", Nephrology News & Issues, pp. 44–55, Jun. 1993, Jackson, MS.

Gambro, "FAM 10 Fistula Flow Studies and Their Interpretation", pp. 1–31, Lund Sweden, published on or before Sep. 29, 1991.

Salamon et al. Translation: low frequency electrodeless conductometer for measuring the electrical conductivity of solutions, 1959, Industrial Group Headquarters, Risley, Warrington, Lancashire, GB.

Richard A. Sherman, "Recirculation Revisited", Seminars in Dialysis, vol. 4, No. 4 pp. 221–223, Oct.–Dec. 1991, New Jersey.

McKamy Smith, "Cardiac Output Determined by the Saline Conductivity Method Using an Extraarterial Conductivity Cell", Cardiovascular Research Center Bulletin, vol. 5, No. 4, pp. 123–134, Apr.–Jun. 1967, Texas.

Mogens Thomsen et al., "Evaluation of Clinical Examination Preceding Surgical Treatment of AV–Fistula Problems," Acta Chir Scand, vol. 151, pp. 133–137, 1985, Sweden.

Transonic Systems, Inc., Access Flow & Recirculation Measured During Hemodialysis, Oct. 1994, N.Y.

C. Aldridge et al., "The Assessment of Arteriovenous Fistulae Created for Hemodialysis from Pressure and Thermal Dilution Measurements, Journal of Medical Engineering & Technology," vol. 8, No. 3, pp. 118–124, May/Jun. 1984, U.K.

C. Aldridge, et al., "Instrument Design for the Bedside Assessment of Arteriovenous Fistulae in Hemodialysis Patients," Proceedings EDTNA–ERCA, vol. 14, pp. 255–260, 1985, U.K.

Joseph J. Carr, "Integration of Decaying Exponential Sensor Output Signals", Sensors, pp. 28–34, Jul. 1989, Virginia.

J. Daugirdas, "The Fourth Annual Advanced Dialysis Technical Symposium", Dialysis & Transplantation, vol. 17, No. 8, pp. 432–433, Aug. 1988, Illinois.

Fresenius, "BTM 4008", Nov. 1993, Germany and translation from German to English.

Gambro, "Fistula Assessment Monitor FAM10," approximately 1985, U.K.

Gambro, "Fistula Assessment Monitor FAM10 Operator's Manual," approximately 1985, U.K.

Krivitski et al., "Accuracy of Dilution Techniques for Access Flow Measurement During Hemodialysis," American Journal of Kidney Diseases, vol. 31, 3 (Mar.) 1998: pp. 502–508.

Krivitski et al., "Development of a Method for Measuring Hemodialysis Access Flow: From Idea to Robust Technology," Seminars In Dialysis vol. 11, 2 (Mar.–Apr.) 1998: pp. 124–230.

Man et al, "Clinical Validation of a Predictive Modeling Equation for Sodium", Artificial Organs, vol. 9, No. 2, 1985, pp. 150–154.

* cited by examiner

METHOD AND DEVICE FOR MEASURING ACCESS FLOW

This application claims the benefit of U.S. Provisional Application No. 60/105,396 filed Oct. 23, 1998.

AREA OF INVENTION

The present invention relates to a method and device for measuring blood flow rate in a blood access. Blood is taken out from the body of a mammal to an extracorporeal blood circuit through a blood access, via needles or a catheter.

PRIOR ART

There are several types of treatments in which blood is taken out in an extracorporeal blood circuit. Such treatments involve, for example, hemodialysis, hemofiltration, hemodiafiltration, plasmapheresis, blood component separation, blood oxygenation, etc. Normally, blood is removed from a blood vessel at an access site and returned to the same blood vessel or at another location in the body.

In hemodialysis and similar treatments, an access site is commonly surgically created in the nature of a fistula. Blood needles are inserted in the area of the fistula. Blood is taken out from the fistula via an arterial needle and blood is returned to the fistula via a venous needle.

A common method of generating a permanent access site having capability of providing a high blood flow and being operative during several years and even tens of years, is the provision of an arterio-venous fistula. It is produced by operatively connecting the radial artery to the cephalic vein at the level of the forearm. The venous limb of the fistula thickens during the course of several months, permitting repeated insertion of dialysis needles.

An alternative to the arterio-venous fistula is the arterio-venous graft, in which a connection is generated from, for example, the radial artery at the wrist to the basilic vein. The connection is made with a tube graft made from autogenous saphenous vein or from polytetrafluorethylene (PTFE, Teflon). The needles are inserted in the graft.

A third method for blood access is to use a silicon, dual-lumen catheter surgically implanted into one of the large veins.

Further methods find use in specific situations, like a no-needle arterio-venous graft consisting of a T-tube linked to a standard PTFE graft. The T-tube is implanted in the skin. Vascular access is obtained either by unscrewing a plastic plug or by puncturing a septum of said T-tube with a needle. Other methods are also known.

During hemodialysis, it is desirable to obtain a constant blood flow rate of 150–500 ml/min or even higher, and the access site must be prepared for delivering such flow rates. The blood flow in an AV fistula is often 800 ml/min or larger, permitting delivery of a blood flow rate in the desired range.

In the absence of a sufficient forward blood flow, the extracorporeal circuit blood pump will take up some of the already treated blood entering the fistula via the venous needle, so called access or fistula recirculation, leading to poor treatment results.

The most common cause of poor flow with AV fistulas is partial obstruction of the venous limb due to fibrosis secondary to multiple venipunctures. Moreover, stenosis causes a reduction of access flow.

When there is a problem with access flow, it has been found that access flow rate often exhibit a long plateau time period with reduced but sufficient access flow, followed by a short period of a few weeks with markedly reduced access flow leading to recirculation and ultimately access failure. By constantly monitoring the evolution of the access flow during consecutive treatment sessions, it is possible to detect imminent access flow problems.

Several methods have been suggested for monitoring recirculation and access flow. Many of these methods involve injection of a marker substance in blood, and the resultant recirculation is detected. The methods normally involve measurement of a property in the extracorporeal blood circuit. Examples of such methods can be found in U.S. Pat. Nos. 5,685,989, 5,595,182, 5,453,576, 5,510,716, 5,510,717, 5,312,550, etc.

Such methods have the disadvantage that they cannot detect when the access flow has decreased to such an extent that recirculation is at risk, but only when recirculation prevails. Moreover, it is a drawback that injection of a substance is necessary.

A noninvasive technique that allows imaging of flow through AV grafts is color Doppler ultrasound. However, this technique requires expensive equipment.

The measurement of access flow rate necessitates the reversal of the flows in the extracorporeal circuit. A valve for such reversal is shown in i.a. U.S. Pat. Nos. 5,605,630 and 5,894,011. However, these valve constructions comprise dead ends in which blood may stand still for a long time and coagulate, which is a drawback.

DISCLOSURE OF INVENTION

An object of the present invention is to provide a method and a device for measuring the access flow rate without interfering with the blood and without injecting a substance in blood.

Another object of the invention is to provide a method and a device for measuring access flow rate without measuring on the blood in the extracorporeal blood circuit or in the access or blood vessel.

According to the invention, it is required to reverse the blood flow through the access. Thus, a further object of the invention is to provide a valve for reversing the blood flow.

A still further object of the invention is to provide a method for determining when the blood flow rate is so small that risk for recirculation prevails.

These objects are achieved with a method and an apparatus for estimating fluid flow rate (Qa) in a fluid flow access, comprising removing a first fluid flow from said access at a removal position to an external flow circuit comprising a dialyzer having a semipermeable membrane, said first fluid flow passing along said membrane at one side thereof and a dialysis fluid being emitted from the other side thereof, and returning said first fluid flow from said external flow circuit to said access at a return position downstream of said removal position, measuring a first variable which is essentially proportional to a concentration (Cd norm) of a substance in said dialysis fluid emitted from the dialyzer, reversing the removal position with the return position and measuring a second variable which is essentially proportional to the concentration (Cd rev) of said substance in said dialysis fluid in the reversed position; and calculating the fluid flow rate (Qa) in said flow access from said measured concentrations.

Preferably, the calculation of the fluid flow rate in said flow access takes place by calculating the ratio between the first and the second variable and using the formula: Cd norm/Cd rev=1+K/Qa, in which Cd norm and Cd rev are values proportional to the concentrations of said substance in the dialysis fluid in the normal and reversed positions, respectively, and K is the clearance of the dialyzer and Qa is the access flow rate.

The blood flow access may be in a mammal for obtaining access to a blood vessel, such as a hemodialysis access in the nature of an arterio-venous shunt or fistula. In the latter case, the dialyzer clearance K is replaced by the effective dialyzer clearance Keff obtained by taking into account a cardiopulmonary recirculation and in the normal position.

The substance is preferably selected from the group of: urea, creatinine, vitamin B12, beta-two-microglobuline and glucose, or may be an ion selected from the group of: $Na^+$, $Cl^-$, $K^+$, $Mg^{++}$, $Ca^{++}$, $HCO_3^-$, acetate ion, or any combination thereof as measured by conductivity; and wherein said concentration is measured as the concentration difference between the outlet and the inlet of the dialyzer, if applicable.

It is possible to measure the actual concentration of the substance. However, since only the ratio between the concentrations in the normal and the reversed position, respectively, is needed, it is possible to measure a value which is proportional to the concentration of said substance, whereby said value is used in place of said concentration. Said property may be the blood concentration of said substance in the external circuit, either before or after the dialyzer. Alternatively, the relative whole body efficiency ($K_{wh}/V$) may be used, as explained in more detail below.

The effective clearance Keff may be obtained by the equation Keff=Qd*Cd/Cs, where Qd is the flow of dialysis fluid emitted from the dialyzer, Cd is the concentration of said substance in said dialysis fluid and Cs is the concentration of said substance in systemic venous blood.

A method of measuring the concentration (Cs) of said substance in systemic venous blood comprises the steps of: stopping the blood flow in the external flow circuit for a time period sufficient to allow the cardiopulmonary circulation to equalize; starting the blood flow in the external flow circuit with a slow speed to fill the arterial line with fresh blood before the measurement; and measuring the equalized concentration of said substance in the dialysis fluid at a low dialysate flow rate or at isolated ultrafiltration. It is advantageous to make the measurement of the effective clearance at the initiation of the treatment.

The concentration (Cs) of said substance in systemic venous blood may be estimated by: calculating a whole body mass of urea (Murea) in the body of the patient, estimating or measuring the distribution volume (V) of urea in the body of the patient; and estimating the concentration (Cs) of said substance in the blood by dividing the whole body mass of urea with the distribution volume. In this way, the mean concentration of urea in the whole body is obtained. However, the mean concentration in the whole body is slightly higher than the urea concentration in the systemic blood, except at the start of the treatment. Thus, this calculation should preferably be done or be extrapolated to the start of the treatment.

It is possible to discriminate between the condition when access or fistula recirculation has developed and not. A method for that purpose would be: changing the blood flow rate (Qb); monitoring the concentration of said substance in the dialysate emitted from the dialyzer; and detecting a possible fistula recirculation in the normal position by correlating a change in said concentration to said change of the blood flow rate.

Preferably, the blood flow rate is decreased and a corresponding decrease in the urea concentration is monitored, and the absence of such a decrease being indicative of fistula recirculation.

SHORT DESCRIPTION OF DRAWINGS

Further objects, advantages and features of the invention appears from the following detailed description of the invention with reference to specific embodiments of the invention shown on the drawings, in which.

DESCRIPTION OF DETAILED EMBODIMENTS OF THE INVENTION

For the purpose of this description, an access site is a site in which a fluid in a tube can be accessed and removed from and/or returned to the tube. The tube may be a blood vessel of a mammal, or any other tube in which a fluid is flowing. The access flow rate is the flow rate of the fluid in the tube or blood vessel immediately upstream of the access site or removal position.

Figure 1:
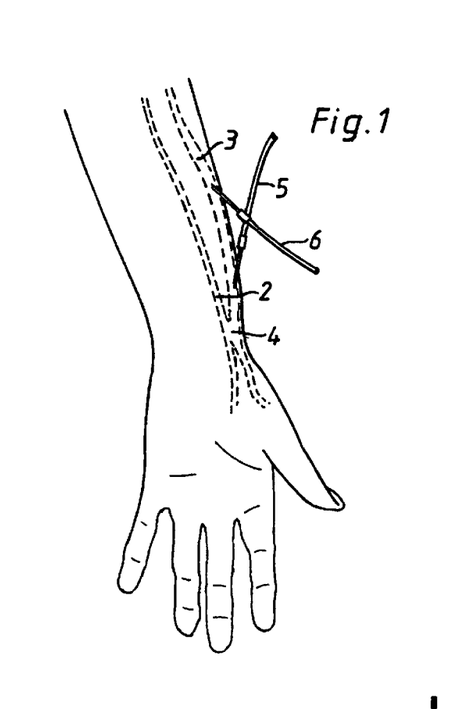
FIG. 1 is a partially schematic view of a forearm of a patient provided with an AV fistula.

FIG. 1 discloses a forearm 1 of a human patient. The forearm 1 comprises an artery 2, in this case the radial artery, and a vein 3, in this case the cephalic vein. Openings are surgically created in the artery 2 and the vein 3 and the openings are connected to form a fistula 4, in which the arterial blood flow is cross-circuited to the vein. Due to the fistula, the blood flow through the artery and vein is increased and the vein forms a thickened area downstream of the connecting openings. When the fistula has matured after a few months, the vein is thicker and may be punctured repeatedly. Normally, the thickened vein area is called a fistula.

An arterial needle 5 is placed in the fistula, in the enlarged vein close to the connected openings and a venous needle 6 is placed downstream of the arterial needle, normally at least five centimeters downstream thereof.

Figure 2:
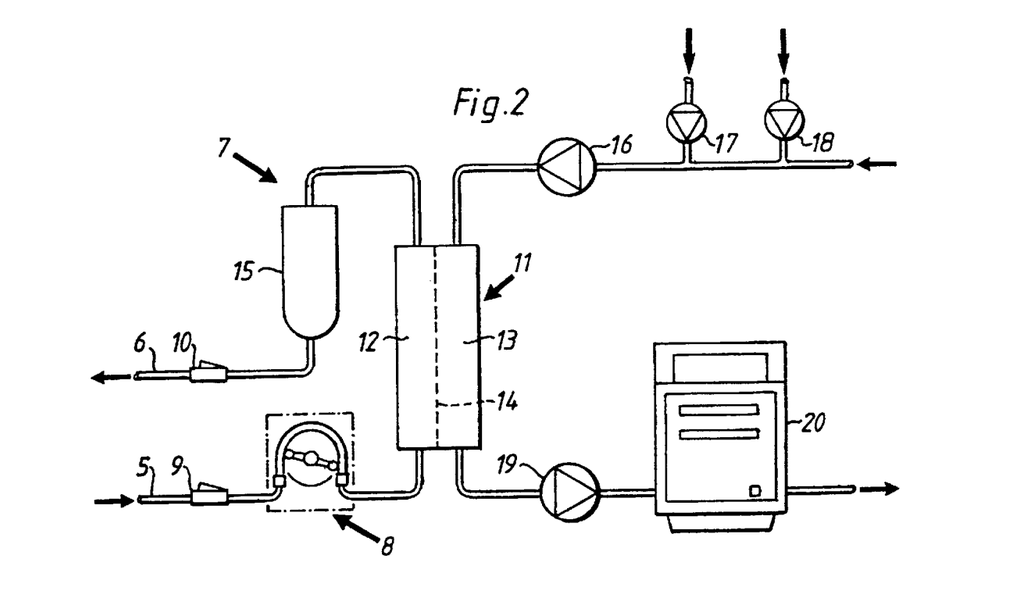
FIG. 2 is a schematic diagram of an extracorporeal dialysis circuit.

The needles 5 and 6 are connected to a tube system 7, shown in FIG. 2, forming an extracorporeal circuit comprising a blood pump 8, such as a dialysis circuit. The blood pump propels blood from the blood vessel, through the arterial needle, the extracorporeal circuit, the venous needle and back into the blood vessel.

The extracorporeal blood circuit 7 shown in FIG. 2 further comprises an arterial clamp 9 and a venous clamp 10 for isolating the patient from the extracorporeal circuit should an error occur.

Downstream of pump 8 is a dialyzer 11, comprising a blood compartment 12 and a dialysis fluid compartment 13 separated by a semipermeable membrane 14. Further downstream of the dialyzer is a drip chamber 15, separating air from the blood therein.

Blood passes from the arterial needle past the arterial clamp 9 to the blood pump 8. The blood pump drives the blood through the dialyzer 11 and further via the drip chamber 15 and past the venous clamp 10 back to the patient via the venous needle. The drip chamber may comprise an air detector, adapted to trigger an alarm should the blood emitted from the drip chamber comprise air or air bubbles. The blood circuit may comprise further components, such as pressure sensors etc.

The dialysis fluid compartment 13 of the dialyzer 11 is provided with dialysis fluid via a first pump 16, which obtains dialysis fluid from a source of pure water, normally RO-water, and one or several concentrates of ions, metering pumps 17 and 18 being shown for metering such concentrates. The preparation of dialysis fluid is conventional and is not further described here.

An exchange of substances between the blood and the dialysis fluid takes place in the dialyzer through the semipermeable membrane. Notably, urea is passed from the blood, through the semipermeable membrane and to the dialysis fluid present at the other side of the membrane. The exchange may take place by diffusion under the influence of a concentration gradient, so called hemodialysis, and/or by convection due to a flow of liquid from the blood to the dialysis fluid, so called ultrafiltration, which is an important feature of hemodiafiltration or hemofiltration.

From the dialysis fluid compartment 13 of the dialyzer is emitted a fluid called the dialysate, which is driven by a second pump 19 via a urea monitor 20 to drain. The urea monitor continuously measures the urea concentration in the dialysate emitted from the dialyzer, to provide a dialysate urea concentration curve during a dialysis treatment. Such urea concentration curve may be used for several purposes, such as obtaining a total body urea mass, as described in WO 9855166, and to obtain a prediction of the whole body dialysis dose Kt/V as also described in said application. The content of WO 9855166 is incorporated in the present specification by reference.

As described above, the present invention provides a method of non-invasively measuring the access flow in the fistula immediately before the arterial needle, using the urea monitor and the dialysis circuit as shown in FIG. 2.

By measuring the dialysis urea concentration during normal dialysis and then reversing the positions of the needles and measuring the dialysis urea concentration with the needles in the reversed position, it is possible to calculate the blood flow in the blood access, without the addition of any substance to blood or the dialysis fluid.

Figure 3:
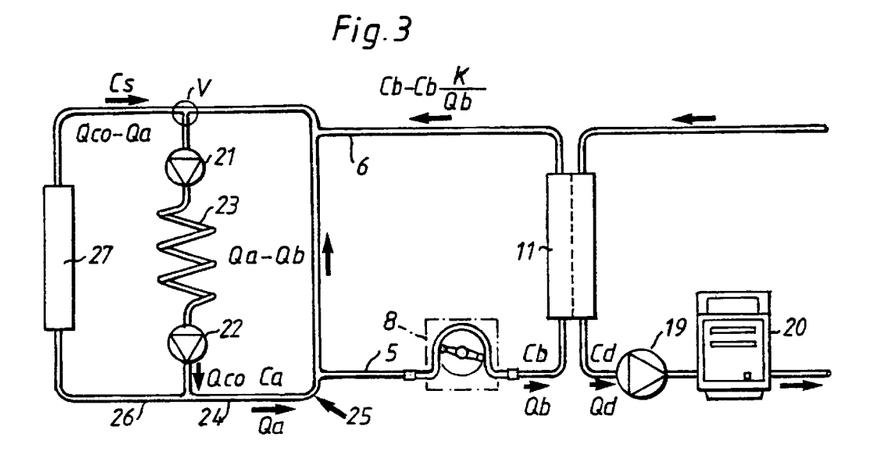
FIG. 3 is a schematic diagram of the blood flow circuit in a patient and in the attached extracorporeal blood circuit.

FIG. 3 shows a simplified schematic diagram of the blood vessel circuit of a patient and a portion of the dialysis circuit according to FIG. 2. The patient blood circuit comprises the heart, where the right chamber of the heart is symbolized by an upper pump 21 and the left chamber of the heart is symbolized by a lower pump 22. The lungs 23 are located between the upper and lower pump. From the outlet of the left chamber pump 22 of the heart, the blood flow divides into a first branch 24 leading to the access 25, normally in the left forearm of the patient, and a second branch 26 leading to the rest of the body, such as organs, other limbs, head, etc. symbolized by a block 27. Blood returning from the body from the organs etc., i.e. from block 27, combines with blood returning from the access and enters the right chamber pump 21.

The cardiac output flow rate is defined as Qco and the flow rate of the access is defined as Qa, which means that Qco-Qa enters the block 27. The venous blood returning from block 27 before being mixed with blood from the access, the systemic venous blood, has a urea concentration of Cs. The blood leaving the left chamber pump 22 has a urea concentration of Ca equal to that passing out to the access 25 as well as to the block 27.

For measuring the access flow rate, it is necessary to reverse the flow through the arterial and venous needles. One way of achieving that is to reverse the needles manually.

Figure 5:
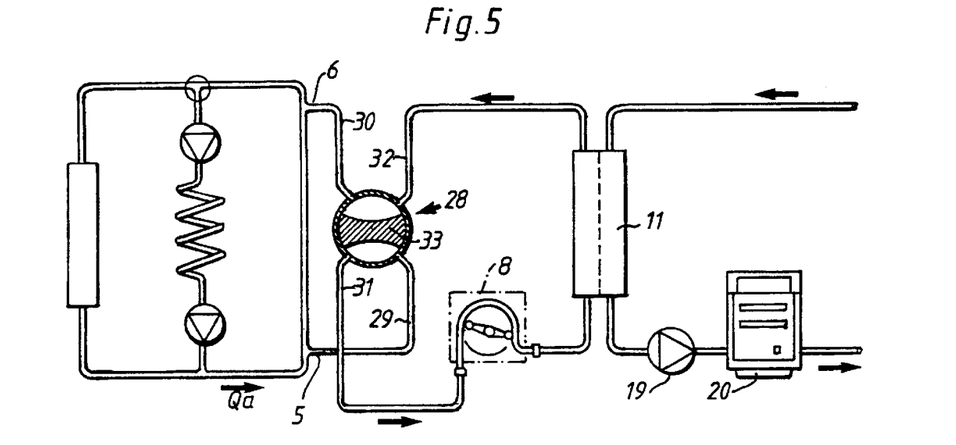
FIG. 5 is a schematic diagram of a blood flow circuit including a switch valve.

Alternatively, FIG. 5 shows a valve 28 for performing the same operation. The arterial needle 5 is connected to an arterial inlet line 29 of the valve and the venous needle 6 is connected to a venous inlet line 30 of the valve. The blood pump is connected to a first outlet line 31 of the valve and the returning blood from the dialyzer 11 is connected to a second outlet line 32 of the valve.

The valve comprises a valve housing and a pivotable valve member 33, which is pivotable from the normal position shown on the drawing to a reverse position pivoted 90° in relation to the normal position.

In the normal position shown in FIG. 5, the arterial needle 5 is connected to the blood pump 8 and the venous needle 6 is connected to the outlet of the dialyzer, via the drip chamber, see FIG. 2. In the reversed position, the arterial needle 5 is connected to the outlet of the dialyzer and the venous needle 6 is connected to the blood pump 8, as required.

Figure 7:
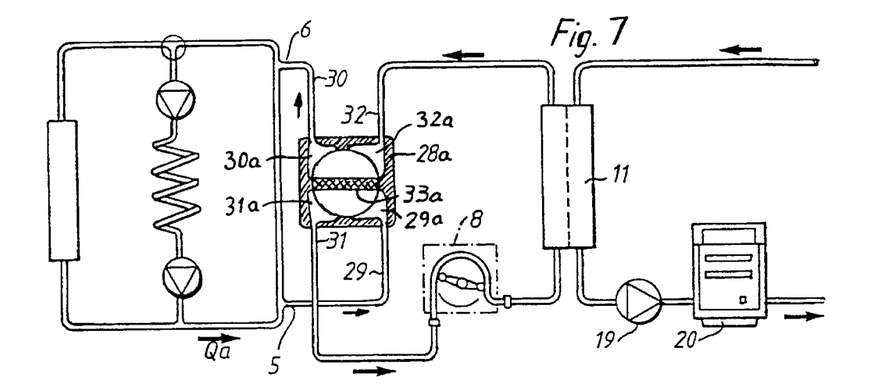
FIG. 7 is a schematic diagram similar to the diagram of FIG. 5 comprising an alternative valve arrangement.
Figure 8:
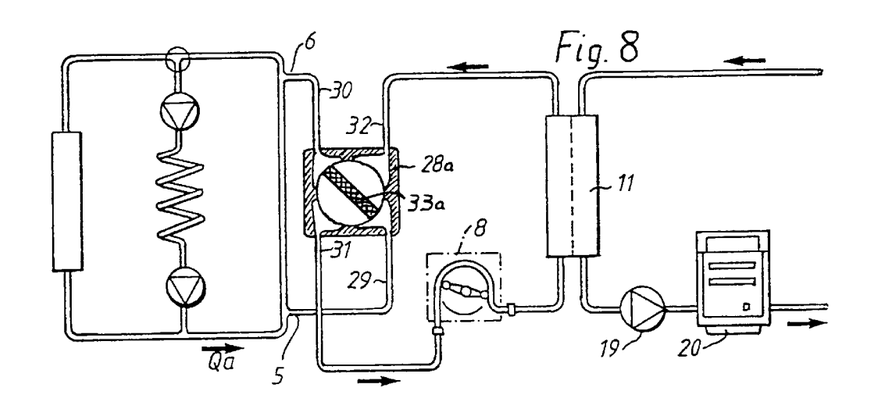
FIG. 8 is a schematic diagram similar to the diagram of FIG. 7 showing the valve arrangement in an idle position.
Figure 9:
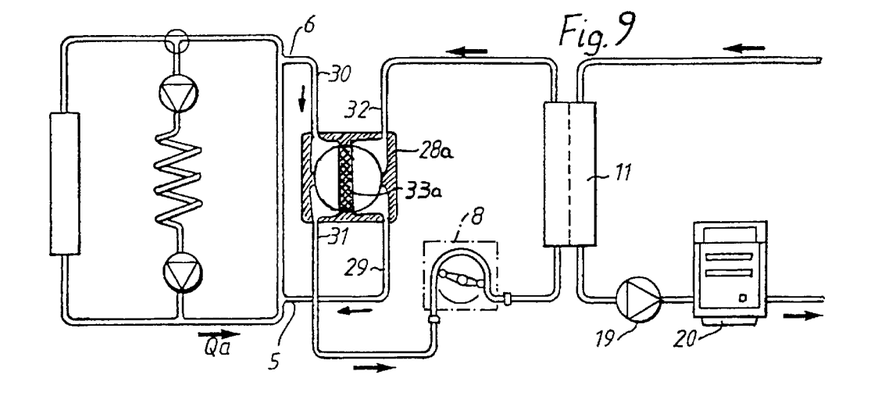
FIG. 9 is a schematic diagram similar to the diagram of FIG. 7 showing the valve arrangement in a reversed position.

An alternative design of the valve arrangement is shown in FIGS. 7, 8 and 9. In the embodiment of FIG. 7, the arterial line 29 is connected to an enlarged opening 29a and the venous outlet line 30 is connected to an enlarged opening 30a, the openings being arranged in the valve housing 28a diametrically opposite to each other. Two enlarged openings 31a and 32a are arranged in the valve housing 28a diametrically opposite each other and displaced 90° in relation to enlarged openings 29a and 30a. The pivotable valve member 33a is normally arranged as shown in FIG. 7 and forms a partition dividing the valve chamber in two semi-circular portions. The valve member has a width, which is smaller than the peripheral dimension of the enlarged openings. The valve member is pivotable 90° to a reverse position, shown in FIG. 9, in which the blood flows through the arterial and venous needles are reversed.

During its movement from the normal to the reversed position, the valve member 33a passes through an idle position shown in FIG. 8, in which all four enlarged openings are interconnected, because the width of the valve member is smaller than the peripheral dimension of the enlarged openings. By this idle position, harm to blood cells may be avoided. Such harm may be caused by high shear stresses which may occur if the inlet line 31 to the blood pump or the outlet line 32 from the dialyzer are completely occluded. By means of the idle position, another advantage is obtained, that the blood needles are not exposed to rapid change of flows, which in some instances even may result in dislocation of the needles. When the valve member is moved from the normal position to the idle position, the flow through the needles change from the normal flow of, for example, 250 ml/min to essentially zero flow. The valve member may be placed in the idle position for some seconds. Then, the valve member is moved to the reversed position, and the flows through the needles are changed from essentially zero flow to—250 ml/min. In this way, a more gentle switch between normal and reversed flows may be obtained.

It is noted, that the positions of the openings and the valve member may be different so that the pivotal movement may be less than or more than 90°. Moreover, the openings need not be arranged diametrically in order to achieve the desired operation. Furthermore, the dimensions of the enlarged openings in relation to the tubes and lines are not in scale, but the diameter of the enlarged openings is rather of the same dimension as the tube inner diameter, as appears more clearly below.

It is noted that the valve is constructed to have as few dead end portions as possible, in which the blood may stand still and coagulate. From the drawing, it is appreciated that no portion of the valve has a dead end construction in any position of the valve body.

Figure 10:
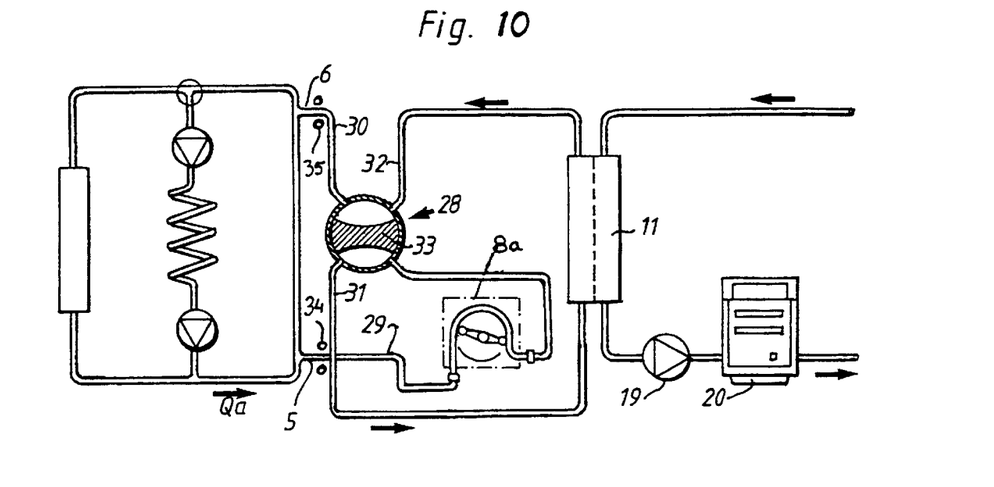
FIG. 10 is a schematic diagram similar to FIG. 5 with the pump in an alternative position.

Furthermore, another schematic diagram incorporating a valve is shown in FIG. 10. FIG. 10 differs from FIG. 5 only in the placement of the pump 8a, which in the embodiment according to FIG. 10 is placed between the arterial needle 5 and the valve 28. In this manner, the pressure across the valve body 33 is less compared to the embodiment according to FIG. 5. The operation is somewhat different. The blood pump is stopped, and the valve is put in the reversed position. Finally, the pump is started and pumping the blood in the opposite direction by reversing the rotational direction of the pump.

In order to ascertain that no air is introduced into the patient in either position of the valve, it may be advantageous to add an air detector 34 and 35 immediately before each of the arterial and venous needle, or at least before the arterial needle. The air detectors trigger an alarm should they measure air bubbles in the blood given back to the blood vessel. Normally, the air detector in the drip chamber is sufficient for this purpose.

Figure 12:
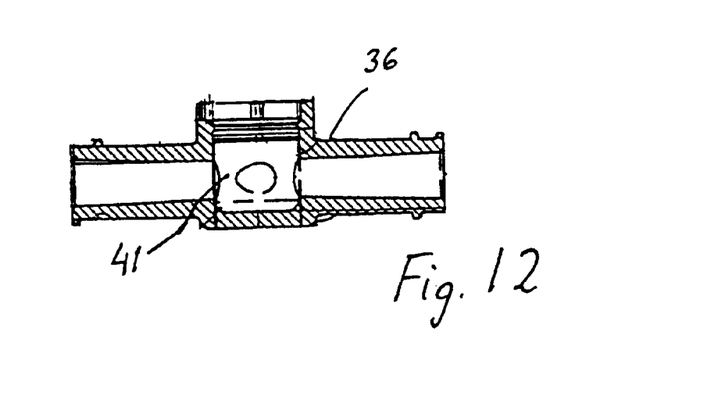
FIG. 12 is a cross-sectional view of a valve housing to be used in the schematic diagram of FIGS. 5 and 7 to 10.
Figure 13:
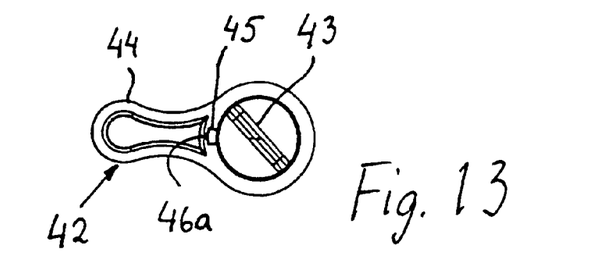
FIG. 13 is a bottom view of a valve member intended to be inserted in the valve housing of FIG. 12.
Figure 14:
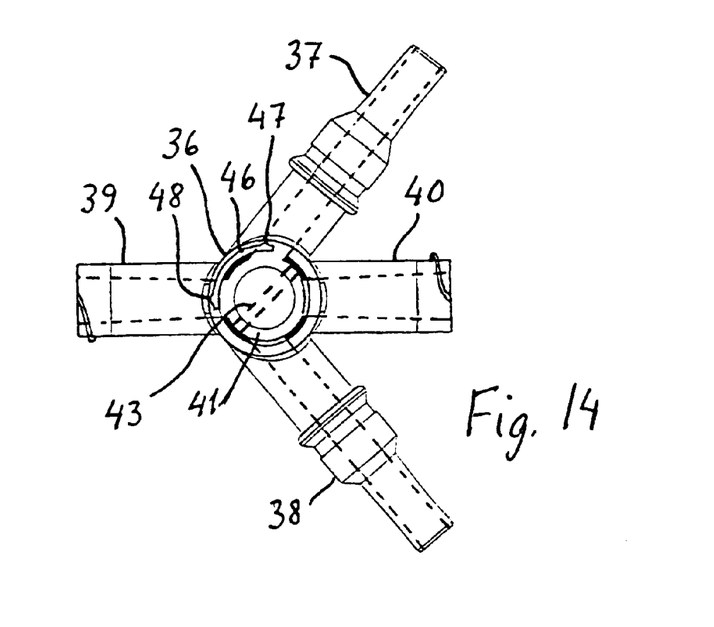
FIG. 14 is a partially schematic plan view of the valve housing of FIG. 12.

The detailed construction of a valve intended to be used in the present invention, is disclosed in FIGS. 12, 13 and 14. The valve comprises a valve housing 36 comprising two inlet connectors and two outlet connectors. All four connectors open into cylindrical valve chamber 41, the four openings being displaced 90° in relation to each other.

As shown in FIG. 14, the valve comprises a blood inlet connector 37 connected to the arterial needle 5 and a blood outlet connector 38 connected to the venous needle 6. The connector portions are arranged as male Luer connectors to be connected to flexible tubes ending with a female Luer connector.

Furthermore, the valve comprises a circuit outlet connector 39 connected to the blood pump 8 and a circuit inlet connector 40 connected to the dialyzer outlet. The connector portions 39 and 40 are arranged as female Luer connectors to mate with male Luer connectors of the circuit.

As appears from FIG. 12, the cylindrical valve chamber 41 is closed at the bottom. From the top, a valve member 42 may be introduced into the cylindrical valve chamber. The valve member 42 comprises a valve partition 43 as appears from FIG. 13.

The valve member also comprises an operating wing 44, by means of which the valve member may be pivoted 90° between a normal position, in which the valve partition 43 is situated as shown by dotted lines in FIG. 14, and a reversed position. The pivotal movement is limited by a shoulder 45 of the valve member 42, which cooperates with a groove 46 in the valve housing. The shoulder 45 is provided with a protrusion 46a which cooperates with two recesses 47 and 48 in the normal position and reverse position, respectively, to maintain the valve member in either position. The groove 46 may be provided with a third recess (not shown in the drawing) in order to define said idle position. Such a third recess is positioned in the middle between the two recesses 47 and 48.

The valve member and housing are provided with suitable sealing to ensure safe operation. The operation of the valve is evident from the above description.

By studying the theoretical dialysate urea concentrations resulting from a given dialyzer clearance K, a given access blood flow Qa and a given blood urea concentration Cs in the systemic venous blood returning from the body, it is found that the effective urea clearance Keff of the dialyzer, taking the cardiopulmonary recirculation into account, is needed for the calculation of access flow. The effective clearance can be measured, for example as described in EP 658 352, the contents of which is incorporated in the present application by reference.

Alternatively, the effective clearance can be calculated from simultaneous systemic venous blood Cs and dialysate Cd measurements of urea concentrations, such as by blood samples.

The systemic blood urea concentration Cs may be measured by the so called stop flow—slow flow technique, where the blood flow is substantially stopped for a couple of minutes to allow the cardiopulmonary recirculation to equalize. Thereafter, the pump is run slowly to fill the arterial line with fresh blood before taking the blood sample. The urea concentration in the so obtained blood sample is equal to the urea concentration Cs in the systemic venous blood returning from the body to the heart.

Alternatively to taking a blood sample, the dialysis fluid flow at the other side of the membrane is stopped and the slowly flowing blood is allowed to equalize with the dialysate at the other side of the membrane, whereupon the urea concentration of the dialysate is measured to obtain the systemic venous blood urea concentration Cs.

A further method to obtain effective clearance is described in WO 9929355. According to the invention described in WO 9929355, the systemic blood concentration Cs is measured before or at the initiation of the treatment, for example by stop flow—slow flow technique with blood sample or equalization as described above. After obtaining valid dialysate urea concentration values Cd from a urea monitor connected to the dialyzer outlet line, the initial dialysate urea concentration $C_{dinit}$ at the start of the treatment is extrapolated by the dialysate urea curve obtained. The content of WO 9929355 is incorporated herein by reference.

A still further method of obtaining systemic blood urea concentration Cs is to calculate the urea mass $M_{wh}$ in the whole body and extrapolate the urea mass to the start of the treatment. By dividing the whole body urea mass $M_{wh}$ with the distribution volume V, the systemic blood urea concentration Cs at the start of the treatment is obtained.

By dividing the dialysate urea concentration Cd with the systemic blood urea concentration Cs and multiplicating with the dialysate flow rate Qd, the effective clearance Keff is obtained. It is advantageous to measure the effective clearance Keff at the initiation of the treatment.

Furthermore, in the method of the invention, the blood flows in the arterial and venous needles are reversed. The dialysate urea concentrations in the two cases with normal position of the needles and with reverse position of the needles may be calculated as follows, with reference to FIGS. 3 and 4.

Figure 4:
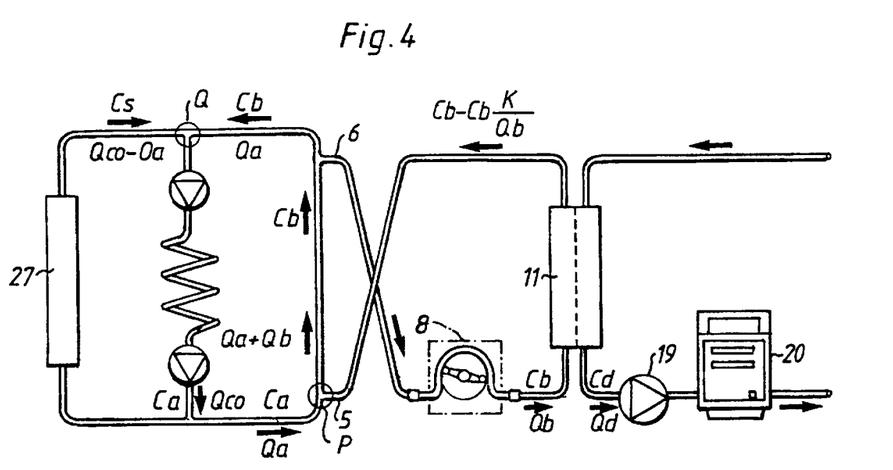
FIG. 4 is a schematic diagram similar to FIG. 3, but with the extracorporeal circuit in an alternative reversed position.

The blood urea concentration Cs in the venous blood returning from the body is assumed unchanged when the lines are reversed, and the dialyzer clearance K is also assumed unchanged. For simplicity ultrafiltration is assumed to be zero, but it is also possible to handle a nonzero UF.

The following notations are used:

Qco—Cardiac Output
Qa—Access flow
Qb—Blood flow in extracorporeal circuit
Qd—Dialysate flow
K—Dialyzer clearance
Keff—Effective dialyzer clearance
Cs—Blood urea concentration in systemic venous blood returning from the body
Ca—Blood urea concentration in the access
Cb—Blood urea concentration at the dialyzer inlet
Cd—Dialysate urea concentration The definition of clearance is:

$$K = \text{(removed urea)}/Cb = Qd*Cd/Cb \quad (1)$$

Consider first the case in which Qa>Qb and the needles are in the normal position. In this case Cb=Ca.

Removal from blood must equal appearance in the dialysate so that $$K*Ca = Qd*Cd \quad (2)$$

A mass balance for urea at the point V, see FIG. 3, when mixing the venous return blood with the blood from the access gives:

$$Ca*Qco = Cs*(Qco-Qa) + Ca*(Qa-K) \quad (3)$$

Thus, we obtain a relation between Ca and Cs.

By combining equations 2 and 3 we obtain:

$$Cd = (K/Qd)*Cs/[1+K/(Qco-Qa)] \quad (4)$$

The definition of effective clearance Keff implies that Cs should be used in the denominator instead of Cb as normally used in dialyzer clearance, which means that $$\text{Keff} = K*(Cb/Cs) = K/[1+K/(Qco-Qa)] \quad (5)$$

If we now turn to the case with reversed lines, see FIG. 4, we still have that what is removed from the blood must enter the dialysate, so that in this case $$K*Cb = Qd*Cd \quad (6)$$

The flow in the fistula between the needles will be Qa+Qb and we can calculate the blood urea concentration at the dialyzer inlet from a urea mass balance at the point P where the dialyzed blood enters the access again $$Cb*(Qb-K) + Ca*Qa = Cb*(Qb+Qa) \quad (7)$$

We also have the mass balance at the point Q where the venous return blood meets the dialyzed blood in the access return flow:

$$Ca*Qco = Cs*(Qco-Qa) + Cb*Qa \quad (8)$$

By eliminating Ca and Cb we get $$Cd = (K/Qd)*Cs/[1+(Qco/Qa)*K/(Qco-Qa)] \quad (9)$$

Since Cs, K and Qd in the two cases are unchanged, it is possible to obtain the ratio of dialysate urea concentrations:

$$Cd\ norm/Cd\ rev = 1 + (K/Qa)/[1 + K/(Qco-Qa)] = \quad (10)$$

$$= 1 + Keff/Qa$$

Figure 6:
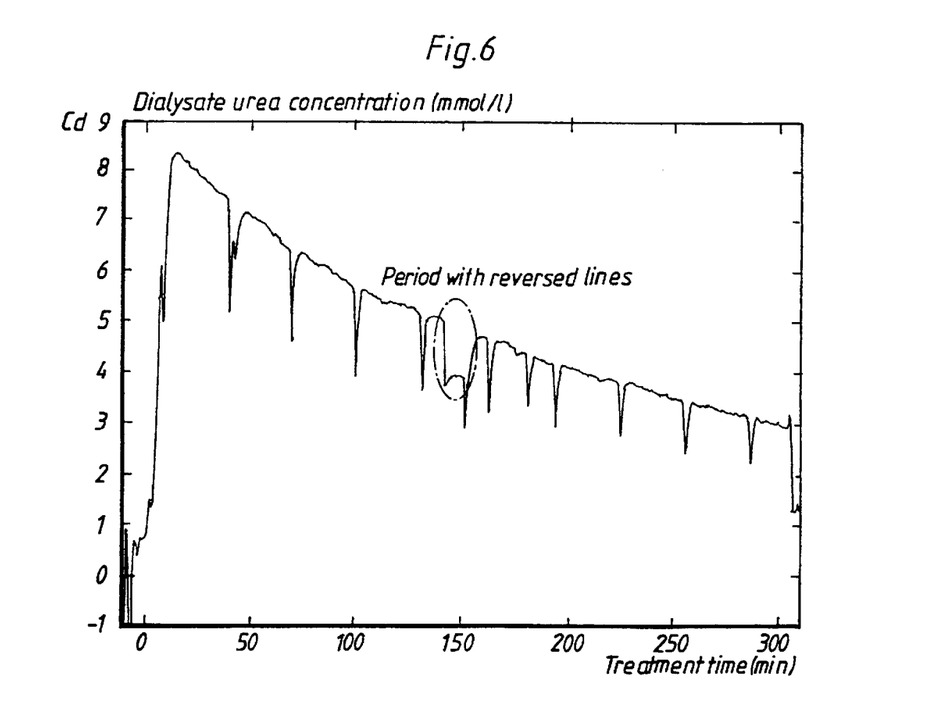
FIG. 6 is a diagram of the dialysis fluid urea concentration versus time, including a portion with reversed flow access according to the invention.

In practice, the two dialysate urea concentrations are probably best found by a curve fit to the dialysate urea curves before and after the switch of lines, with an extrapolation to the time of switching from the respective side, see FIG. 6, which shows the urea concentration Cd of the dialysate during a normal hemodialysis treatment.

During a time period of about 10 minutes, marked with a ring in FIG. 6, the arterial and venous needles are reversed. After an initial time period for allowing the urea monitor to measure accurately, the urea concentration with reversed lines is appr. 0.8 times the original urea concentration, which means that Cdnorm/Cdrev=1.25. Thus, if Keff is 200 ml/min, as measured with the needles in the normal position or estimated as described above, the access flow is 800 ml/min.

The effective clearance may also be obtained as a rough estimate from blood and dialyzer flows and dialyzer characteristics, e.g. from the dialyzer date sheet.

In the present specification, there are used three different clearances, namely dialyzer clearance, effective clearance and whole body clearance. If dialyzer clearance is 250 ml/min for a certain blood flow rate and dialysate flow rate, the effective clearance is normally 5 to 10% lower, such as 230 ml/min. The whole body clearance is still 5 to 15% lower, such as 200 ml/min. The dialyzer clearance is the clearance as measured directly on the dialyzer. The effective clearance is the clearance also taking into account the cardio-pulmonary recirculation. Finally, the whole body clearance is the effective clearance further taking into account other membranes in the body restricting the flow of urea from any part of the body to the dialysate. The concept of whole body clearance is described in WO 9855166, the content of which is herewith incorporated by reference.

The effective clearance used in the formula may also be obtained from a measurement according to the method described in EP 658 352 mentioned above, with the needles in the normal position. This will give a measure of the effective plasma water urea clearance, which then has to be converted to whole blood clearance. The method of EP 658 352 essentially comprises that the conductivity of the dialysis fluid upstream of the dialyzer is increased by for example 10% and then returned to the original value. The result at the outlet side of the dialyzer is measured and results in a measure of the effective clearance Keff of the dialyzer.

Alternatively, the effective clearance may be calculated according to equation Keff=Qd*Cd/Cs. The systemic venous urea concentration may be measured at the same time as the dialysate urea concentration Cd, or by the methods described above.

Another method would be to use the value of total body urea mass Murea obtained by the method according to WO 9855166, mentioned above. By obtaining the urea distribution volume V by Watson's formula or any other method, the venous urea concentration would be approximately:

$$Cs = \text{Murea}/V \quad (11)$$

In the method of WO 9855166, the relative whole body efficiency of the dialyzing process $K_{wb}/V$ is obtained. Note, that whole body clearance is used, as indicated by the subscript wb. According to said WO 9855166, urea concentration is proportional to the relative whole body efficiency according to the formula:

$$K_{wb}/V = (Q_d \cdot C_d)/m \quad (12)$$

Thus, if ($K_{wb}/V$) is used instead of Cd in the above equation (10), a similar result is obtained, if it is presumed that m is constant, i.e. the measurement must be extrapolated to the same time instance:

$$(K_{wb}/V)\text{norm}/(K_{wb}/V)\text{rev} = 1 + \text{Keff}/Qa \quad (13)$$

As is mentioned in said WO 9855166, it is possible to calculate the relative whole body efficiency only from dialysate urea measurement. Since we are interested only in the ratio in the normal and reversed position, we do not need to calculate the actual $K_{wh}$.

Figure 11:
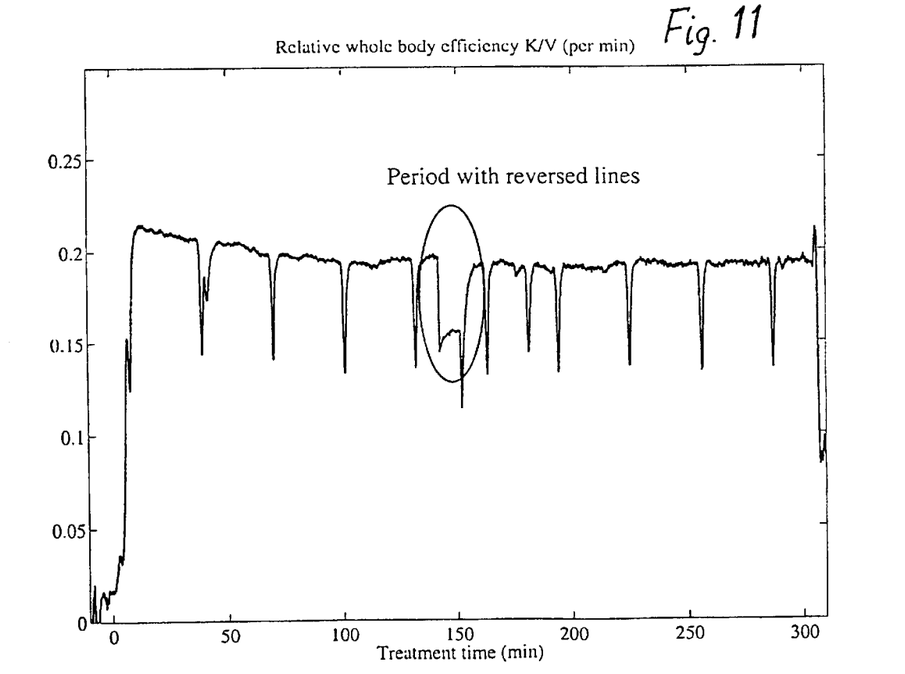
FIG. 11 is a diagram showing calculations with relative whole body efficiency.

FIG. 11 shows a plot of the relative whole body efficiency K/V (min$^{-1}$). The period with reversed lines is shown inside a circle. In all other respects, the same discussion applies as is given above.

The calculations above assume that the extracorporeal blood flow rate Qb does not exceed the access flow rate Qa. If this is the case there will be access recirculation and the flow in the access will be reversed when the needles are in the normal position. The calculation of dialysate urea concentration is unchanged for the needles in reversed position, but has to be modified for the needles in normal position. Calculations corresponding to those above show that the ratio above between dialysate urea concentrations for normal and reversed needle positions will be:

$$Cd \text{ norm}/Cd \text{ rev} = 1 + \text{Keff}/Qb \quad (14)$$

where Keff is the effective clearance with the effect of recirculation included, that is with the needles in the normal position.

The only difference is that the calculation will now give the extracorporeal blood flow Qb instead of the access flow. This blood flow is known, so in practice this means that when the result is an access flow rate Qa close to the blood flow rate Qb, recirculation should be suspected, and this always means that the access has to be improved.

Keff/Qb is a figure lower than one, normally for example 0.6–0.9. Keff/Qa should be considerably lower, for example 0.1–0.4. Thus, when Cd norm/Cd rev approaches or is lower than a predetermined number, such as 1.2 or 1.5, further calculations should be done for determining if access recirculation is present.

A simple procedure is to decrease the blood flow Qb somewhat. If the dialysate concentration then decreases, this means that there is no access or fistula recirculation at least at the lower blood flow.

The above calculations can also be made for the situation where ultrafiltration is present. However, it is a simple measure to reduce the ultrafiltration to zero during the measurement interval. Moreover, the error induced by ultrafiltration is small and may be neglected.

The measurement should be performed during a time interval, which is considerably larger than 30 seconds so that cardio-pulmonary recirculation has been developed. The measurement time for obtaining valid results may be 5 minutes with the needles reversed, while measurements with the needles in correct position may be done in 5 minutes or continuously during the treatment.

The method is also applicable to the methods of treatment comprising infusion of a dialysis solution to the blood before or after the dialyzer, called hemofiltration and hemodiafiltration. The result is the same as given above.

If the access is a venous catheter, there is no cardio-pulmonary recirculation and the calculations becomes simpler. The result is the same, except that the effective clearance Keff is replaced by the dialyzer clearance K, since the systemic venous urea concentration Cs becomes the same as the dialyzer inlet urea concentration Cb.

It should be noted that all flow rates, clearances and urea concentrations in the calculations relate to whole blood. Approximately 93% of plasma is water, depending on the protein concentration, and about 72% of erythrocytes is water. Depending on the hematocrit value, the blood water volume is 10–13% lower than the volume of whole blood, see for example Handbook of Dialysis, Second Edition, John T. Daugirdas and Todd. S Ing, 1994, page 18.

The effective urea clearance obtained according to EP 658 352 relates to blood water, and must therefore be increased by 10–13% before being used in the present formulas. Blood urea concentration values obtained from a laboratory relate in general to plasma, and must therefore be decreased by about 7% in order to relate to whole blood.

Alternatively, all urea concentrations, flow rates and clearances may be used as relating to blood water. The effective clearance is then used unchanged, but the calculated access flow will relate to blood water, and has to be increased by 10–13% to relate to whole blood.

The invention has been described above with reference to use in the human body and using urea as a marker for measuring access flow. However, any other substance present in blood and which can be measured at the dialysate side of the dialyzer may be used according to the invention, such as creatinine, vitamin B12, beta-two-microglobuline, NaCl or any combination of ions. Another alternative is to measure conductivity.

It is also possible to measure a property proportional to the concentration, since it is the ratio that is involved in the equations. Thus, urea concentration may be measured by measuring conductivity differences after passing the urea containing fluid through a urease column, and such conductivity difference can be used directly in place of the concentration values in the equations.

Other indirect methods of measuring any of the above-mentioned substances concentrations may be used as long as the measurements are made at the dialysate side of the dialyzer. Another alternative is to measure the blood urea concentrations by any known method, either before or after the dialyzer, since these concentrations are proportional to the concentrations in the formulas.

The invention has been described above with reference to use in the human body. However, the invention can be used in any tube system where a fluid is passed and a portion thereof is taken out for dialysis, such as in beer or wine production.

What is claimed is:

1. A method of estimating fluid flow rate (Qa) in a fluid flow access, comprising:

removing a first fluid flow from said access at a removal position to an external flow circuit comprising a dialyzer having a semipermeable membrane, said first fluid flow passing along said membrane at one side thereof and a dialysis fluid being emitted from the other side thereof, and returning said first fluid flow from said external flow circuit to said access at a return position downstream of said removal position;

measuring a first variable which is essentially proportional to a concentration (Cd norm) of a substance in said dialysis fluid emitted from the dialyzer;

reversing the removal position with the return position and measuring a second variable which is essentially proportional to the concentration (Cd rev) of said substance in said dialysis fluid in the reversed position; and calculating the fluid flow rate (Qa) in said flow access from said measured concentrations.

2. The method of claim 1, wherein calculating the fluid flow rate in said flow access takes place by the formula:

$$Cd\ norm/Cd\ rev = 1 + K/Qa$$

in which Cd norm and Cd rev are values proportional to the concentrations of said substance in the dialysis fluid in the normal and reversed positions, respectively, and K is the clearance of the dialyzer and Qa is the access flow rate.

3. The method as claimed in claim 2, wherein said flow access is a blood flow access in a mammal for obtaining access to a blood vessel.

4. The method as claimed in claim 3, wherein said flow access is a hemodialysis access in the nature of an arterio-venous shunt or fistula, and wherein the dialyzer clearance K is replaced by the effective dialyzer clearance Keff obtained by taking into account a cardiopulmonary recirculation and in the normal position.

5. The method of claim 4, wherein said Keff is obtained by the equation $$Keff = Qd*Cd/Cs$$

where Qd is the flow of dialysis fluid emitted from the dialyzer, Cd is the concentration of said substance in said dialysis fluid and Cs is the concentration of said substance in systemic venous blood.

6. The method of claim 5, wherein the concentration (Cs) of said substance in systemic venous blood is measured by:
stopping the blood flow in the external flow circuit for a time period sufficient to allow the cardiopulmonary circulation to equalize;
starting the blood flow in the external flow circuit with a slow speed to fill the arterial line with fresh blood before the measurement;
measuring the equalized concentration of said substance in the dialysis fluid at a low dialysate flow rate or at isolated ultrafiltration.

7. The method of claim 5, wherein the concentration (Cs) of said substance in systemic venous blood is estimated by:
calculating a whole body mass of urea (Murea) in the body of the patient,
estimating or measuring the distribution volume (V) of urea in the body of the patient;
estimating the concentration (Cs) of said substance in the blood by dividing the whole body mass of urea with the distribution volume.

8. The method of claim 1, wherein said substance is selected from the group of: urea, creatinine, vitamin B12, beta-two-microglobuline and glucose.

9. The method of claim 8, wherein the measuring step is performed by measuring a property which is proportional to the concentration of said substance, whereby said property is used in place of said concentration.

10. The method of claim 9, wherein said property is anyone of: the blood concentration of said substance in the external circuit; and the relative whole body efficiency ($K_{wh}/V$).

11. The method of claim 1, wherein said substance is an ion selected from the group of: $Na^+$, $Cl^-$, $K^+$, $Mg^{++}$, $Ca^{++}$, $HCO_3^-$, acetate ion, or any combination thereof as measured by conductivity; and said concentration is measured as the concentration difference between the outlet and the inlet of the dialyzer.

12. The method of claim 1, further comprising:
changing the blood flow rate (Qb);
monitoring the concentration of said substance in the dialysate emitted from the dialyzer;
detecting a possible fistula recirculation in the normal position by correlating a change in said concentration to said change of the blood flow rate.

13. The method of claim 12, wherein the blood flow rate is decreased and a corresponding decrease in the urea concentration is monitored, and the absence of such a decrease being indicative of fistula recirculation.

14. An apparatus for extracorporeal blood treatment comprising:
a dialyzer having first and second compartments separated by a semi-permeable membrane;
a blood circuit having;
a blood removal line for connecting, in a normal condition, an inlet of the first chamber to a blood access of a patient at a first connecting point, and
a blood return line for connecting, in the normal condition, an outlet of the first compartment to the blood access of the patient at a second connecting point;
a reversal means for switching the connection of the blood removal line and blood return line to the blood access so that, in a reverse condition, the first connecting point is in fluid communication with the outlet of the first chamber and the second connecting point is in fluid communication with the inlet of the first chamber;
a dialysis liquid circuit having:
a dialysis liquid line for supplying a dialysis liquid to an inlet of the second compartment, and
a dialysate line for draining a dialysate from an outlet of the second compartment;
a sensor connected to the dialysate line for measuring, in the normal condition, a first variable in the dialysate, and for measuring, in the reverse condition, a second variable in the dialysate, the first variable being essentially proportional to a first concentration (Cd norm) of a substance in the dialysate and the second variable being essentially proportional to a second concentration (Cd rev) of the substance in the dialysate;
a calculating means for calculating a fluid flow rate (Qa) in the blood access from the first and second variables and from a clearance of the dialyzer.

15. The apparatus of claim 14, wherein the calculating means calculates the fluid flow rate in the blood access by the formula:

$$Cd\ norm/Cd\ rev = 1 + K/Qa$$

in which Cd norm and Cd rev are values proportional to the concentrations of said substance in the dialysate in the normal and reversed positions, respectively, and K is the clearance of the dialyzer and Qa is the access flow rate.

16. The apparatus as claimed in claim 15, wherein the blood access is a hemodialysis access in the nature of an arterio-venous shunt or fistula, and wherein the dialyzer clearance K is replaced by the effective dialyzer clearance Keff obtained by taking into account a cardiopulmonary recirculation.

17. The apparatus of claims 16, wherein said clearance Keff is obtained by the equation $$Keff = Qd * Cd/Cs$$

where Qd is the flow of dialysate, Cd is the concentration of said substance in said dialysate and Cs is the concentration of said substance in systemic venous blood.

18. The apparatus of claim 17, further comprising means for measuring the concentration (Cs) of said substance in systemic venous blood, including:
- means for stopping a blood flow in the blood circuit for a time period sufficient to allow the cardiopulmonary circulation to equalize and stopping the flow of dialysis fluid;
- means for starting the blood flow in the external flow blood circuit with a slow speed to fill the blood removal line with fresh blood before the measurement;
- means for measuring an equalized concentration of said substance in the dialysate at a low dialysate flow rate or at isolated ultrafiltration.

19. The apparatus of claim 17, further comprising means for estimating the concentration (Cs) of said substance in systemic venous blood, including:
- means for calculating a whole body mass of urea (Murea) in the body of the patient,
- means for estimating or measuring the distribution volume (V) of urea in the body of the patient;
- means for estimating the concentration (Cs) of said substance in the blood by the formula by dividing the whole body mass of urea with the distribution volume.

20. The apparatus of claim 14, wherein said substance is selected from the group of: urea, creatinine, vitamin B12, beta-two-microglobuline and glucose.

21. The apparatus of claim 14, wherein said substance is an ion selected from the group of: $Na^+$, $Cl^-$, $K^+$, $Mg^{++}$, $Ca^{++}$, $HCO_3^-$, acetate ion, or any combination thereof as measured by conductivity; and said concentration is measured as the concentration difference between the outlet and the inlet of the dialyzer.

22. The apparatus of claim 14, wherein the measuring means is adapted to measure a property which is proportional to the concentration of said substance, whereby said property is used in place of said concentration.

23. The apparatus of claim 22, wherein said property is anyone of: the blood concentration of said substance in the blood circuit and the relative whole body efficiency ($K_{wh}/V$).

24. The apparatus of claim 14, further comprising:
- means for changing a blood flow rate (Qb);
- means for monitoring the concentration of said substance in the dialysate;
- means for detecting a possible fistula recirculation in the normal position by correlating a change in said concentration to said change of the blood flow rate.

25. The apparatus of claim 24, comprising means for decreasing the blood flow rate and means for monitoring a corresponding decrease in the urea concentration, whereby the absence of such a decrease being indicative of fistula recirculation.

26. The apparatus of claim 14, wherein said reversal means comprises
a valve means arranged between the blood removal line and the dialyzer and between the blood returning line and the dialyzer for reversing a blood flow direction through the blood removal line and the blood returning line, said valve means comprising two inlet and two outlet openings and a valve member, said valve member being arranged to adopt an idle position in which all four inlet and outlet openings are interconnected.

27. The apparatus of claim 26, further comprising an air detector arranged between the valve means and at least one of the first connecting point and the second connecting point.

* * * * *